United States Patent

Otterholm et al.

Patent Number: 5,145,601
Date of Patent: Sep. 8, 1992

[54] FERROELECTRIC LIQUID CRYSTALS WITH NICOTINIC ACID CORES

[75] Inventors: Bengt Otterholm, Goteborg, Sweden; David M. Walba, Boulder, Colo.

[73] Assignee: The University of Colorado Foundation Inc., Boulder, Colo.

[21] Appl. No.: 542,838

[22] Filed: Jun. 25, 1990

[51] Int. Cl.$^5$ .................. C09K 19/34; C07D 211/72; C07D 211/82
[52] U.S. Cl. ............................. 252/299.61; 546/301; 546/339
[58] Field of Search ................ 252/299.61; 546/301, 546/339

[56] References Cited

U.S. PATENT DOCUMENTS

| | | | |
|---|---|---|---|
| 3,925,237 | 12/1975 | Ross et al. | 252/299.62 |
| 4,293,698 | 10/1981 | Toriyana et al. | 546/301 |
| 4,795,587 | 1/1989 | Ohno et al. | 252/299.61 |
| 4,826,979 | 5/1989 | Kano | 544/224 |
| 4,835,274 | 5/1989 | Kano | 544/239 |
| 4,865,763 | 9/1989 | Inoue et al. | 252/299.61 |
| 4,874,544 | 10/1989 | Yong et al. | 252/299.61 |
| 4,876,026 | 10/1989 | Saito et al. | 252/299.61 |
| 4,886,622 | 12/1989 | Miyazawa et al. | 252/299.61 |

FOREIGN PATENT DOCUMENTS

| | | | |
|---|---|---|---|
| 0263437 | 10/1987 | European Pat. Off. | |
| 0193940 | 10/1985 | Japan | 546/290 |
| 2038823 | 7/1980 | United Kingdom | |
| 8705015 | 8/1987 | World Int. Prop. O. | |
| 8910356 | 11/1989 | World Int. Prop. O. | |

OTHER PUBLICATIONS

Furukawa et al. (1988) Ferroelectrics 85:451-459.
Terashima, K. et al. (1986) Mol. Cryst. Liq. Cryst. 141:237.

Primary Examiner—Robert L. Stoll
Assistant Examiner—C. Harris
Attorney, Agent, or Firm—Greenlee & Winner

[57] ABSTRACT

Liquid crystal and ferroelectric liquid crystal compounds having core moieties based on nicotinic acid and having the general formula:

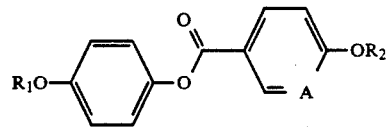

where A is N or N—O and where $R_1$ and $R_2$, independently of one another, are straight chain or branched alkyl groups having from 1 to 20 carbons are provided. Ferroelectric liquid crystals of the present invention include those compounds in which one of $R_1$ or $R_2$ are chiral nonracemic groups. The pyridines and pyridine n-oxides or the present invention are useful as components of liquid crystal materials and certain of these compounds are useful as components of ferroelectric liquid crystal materials.

37 Claims, No Drawings

FERROELECTRIC LIQUID CRYSTALS WITH NICOTINIC ACID CORES

This invention was made with at least partial support of the United States Government which has certain rights in this invention.

FIELD OF THE INVENTION

The present invention relates to liquid crystal compounds which are pyridine-5-carboxylic acid esters and pyridine N-oxide-5-carboxylic acid esters which have application in liquid crystal-based devices, particularly in ferroelectric liquid crystal devices useful in electro-optical and display applications.

BACKGROUND OF THE INVENTION

Liquid crystals have found use in a variety of electro-optical and display device applications, in particular those which require compact, energy-efficient, voltage-controlled light valves such as watch and calculator displays. These devices are based upon the dielectric alignment effects in nematic, cholesteric and smectic phases of the liquid crystal compound in which, by virtue of dielectric anisotropy, the average molecular long axis of the compound takes up a preferred orientation in an applied electric field. Since the coupling to an applied electric field by this mechanism is rather weak, the resultant electro-optical response time may be too slow for many potential applications.

Liquid crystal displays have a number of unique characteristics, including low voltage and low power of operation, which makes them perhaps the most promising of the non-emissive electro-optical display candidates available with today's technology. However, slow response and insufficient nonlinearity can impose limitations for many potential applications. The requirement for speed may become especially important in proportion to the number of elements which have to be addressed in a device. This may result in increasingly impractical production costs for the potential use of such devices in flat-panel displays for use in video terminals, oscilloscopes, radar and television screens.

It has been shown by N. A. Clark and S. T. Lagerwall in Appl. Phys. Lett. 36:899 (1980) and in U.S. Pat. No. 4,367,924 that electro-optic effects with sub-microsecond switching speeds are achievable using the technology of ferroelectric liquid crystals (FLCs). Some display structures prepared using FLC materials, in addition to the high speed (about 1,000 times faster than currently used twisted nematic devices) reported by these investigators, also exhibit bistable, threshold sensitive switching, making them potential candidates for light modulation devices including matrix addressed light valves containing a large number of elements for passive displays of graphic and pictorial information, as well as for optical processing applications. A recent review of the applications of FLC devices is given by Lagerwall, S. T. and Clarke, N. A. (1989) Ferroelectrics 94:3-62.

Smectic C liquid crystal phases composed of chiral, nonracemic molecules possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions. In ferroelectric liquid crystal display devices, like those of Clark and Lagerwall, appropriate application of an external electric field results in alignment of the molecules in the ferroelectric liquid crystal phase with the applied field. When the sign of the applied field is reversed, realignment or switching of the FLC molecules occurs. This switching can be employed for light modulation. Within a large range of electric field strengths, the switching speed (optical rise time) is inversely proportional to applied field strength and polarization or dipole density (P), and directly proportional to orientational viscosity. Fast switching speeds are then associated with FLC phases which possess high polarization density and low orientational viscosity.

A basic requirement for application of ferroelectric liquid crystals in such devices is the availability of chemically stable liquid crystal compounds or mixtures which exhibit ferroelectric phases (chiral smectic C) over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing smectic C* phases with useful temperature ranges can also be obtained by admixture of chiral, nonracemic compounds, designated ferroelectric liquid crystal dopants into liquid crystal host material (which may or may not be composed of chiral molecules). Addition of the dopant can affect the ferroelectric polarization density and/or the viscosity of the C* phase and thereby affect the switching speed. Desirable FLC dopants are molecules which impart high ferroelectric polarization density to an FLC material without significantly increasing the orientational viscosity of the mixture. The components of FLC mixtures can also be adjusted to vary phase transition temperatures or to introduce desired LC phases.

Thermotropic liquid crystal molecules typically possess structures which combine a rigid core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC materials have been prepared by the introduction of a stereocenter into one of the tails, thus introducing chirality. The first FLC compound to be characterized was DOBAMBC (Meyer et al., supra) which contains a 2-methylbutyl chiral tail. Pure DOBAMBC exhibits a smectic C* phase with a ferroelectric polarization of $-3$ nC/cm$^2$.

There are a number of reports of compounds containing phenylbenzoate, diphenyl, phenylpyrimidine and related cores coupled to chiral tail units which possess monotropic smectic C* phases displaying fast switching speeds at room temperature, or which can be employed as FLC dopants to induce high polarization and fast switching speeds when combined in mixtures with FLC host materials.

The following are exemplary reports of such FLC compounds:

Walba et U.S. Pat. No. 4,556,727 reports phenylbenzoates having non-racemic 2-alkoxy-1-propoxy tails. Eidman and Walba, U.S. Pat. No. 4,777,280 report chiral 1-cyanoalkoxy phenylbenzoates. Walba and Razavi, U.S. Pat. No. 4,695,650 report chirally asymmetric reverse ester phenylbenzoates having chiral 1-haloalkyl tail units.

Ohno et al. (1989) U.S. Pat. No. 4,795,587 refers to liquid crystal compounds exhibiting smectic C phases which contain a phenylpyridine core having the formula:

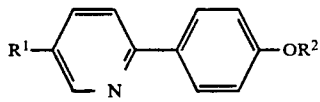

where R¹ is an alkyl group having seven to twelve carbon atoms and R² is an alkyl group having five to twelve carbon atoms.

Japanese patent documents JP 63264573 and JP 62258361 refer to optically active 6-substituted-pyridine-3-carboxylic acid esters useful as ferroelectric smectic liquid crystals. Optically active 6-substituted-pyridine-3-carboxylic acid esters obtained from reaction of dodecyloxybenzoic acid, thionyl chloride and 6-hydroxynicotinic acid (S)-2-methylbutyl ester are specifically referred to. Japanese patent document JP 62175465 refers to ester compounds contained in liquid crystal compositions exhibiting nematic phases. 2-(trans-4-ethyl-cyclohexyl)- 5-nicotinic acid-3-fluoro-4-cyanophenyl ester is referred to specifically.

Walba et al. (1986) J. Amer. Chem. Soc. 108:7424–7425 and Walba and Vohra, U.S. Pat. No. 4,648,073 and U.S. Pat. No. 4,705,874 disclose ferroelectric (chiral) smectic liquid crystal compounds having an achiral core and chiral tail units derived from (2,3)-alkyloxiranemethanols which possess a high ferroelectric polarization density. The ferroelectric liquid crystal materials reported have the following general formulas:

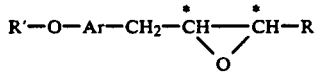

where R is an alkyl of one to seven carbon atoms and R' is an alkyl of five to twelve carbon atoms and Ar is phenylbenzoate or biphenyl.

Hemmerling et al. (1988) European Patent Application, Pub. No. 263437 refers to chiral aryl-2,3-epoxyalkylethers FLC compounds having phenylpyrimidine or phenylpyridazine cores of the formula:

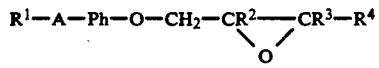

where A is a diazine-2,5,-diyl or diazine-3,6-diyl, R¹ is a straight chain or branched alkyl group having 1-12 carbon atoms wherein one or two non-neighboring CH₂ groups is replaced with an O or S atom, R²⁻⁴ are, independent of one another, H, a straight chain alkyl group having 1-12 carbon atoms or a branched alkyl group having 3-10 carbon atoms wherein R¹, R² and R³ are not all H. Compounds in which R² and R³ are both H having extrapolated polarization densities ($P_{ext}$) in the range from 30-70 nC/cm₂ are reported.

Walba and Razavi, U.S. patent application Ser. No. 099,074, now allowed, discloses chirally asymmetric phenyl and biphenylbenzoates having chiral 2,3-epoxyalkyl or 1-halo-2,3-epoxy alkyl tails which are useful as components of FLC materials. The compounds disclosed have the formula:

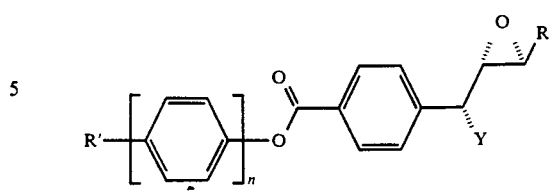

where R' is an alkyl or alkoxy group having three to fifteen carbon atoms, R is an alkyl group having three to fifteen carbon atoms, n=1 or 2, and Y is a halogen or hydrogen. It is also disclosed, therein, that 1-haloepoxides of formula A can impart higher polarization densities and higher switching speeds in FLC mixtures than their diastereomers of formula B. It is suggested that the difference in properties of A and B is due to the relative alignment of the epoxide and halogen bond dipoles in the isomer.

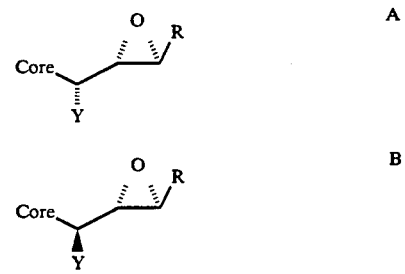

Furukawa, K. et al. (1988) Ferroelectrics 85:451–459 refers to chiral smectic C compounds having an ester group in the core and an optically active tail group, either alkoxy or alkoxy carbonyl, with an electronegative substituent, either a halogen or cyano group, ortho to the chiral tail, for example:

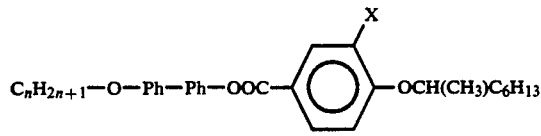

where X=H, Halogen or CN.

Wand et al., USSN 360,397 discloses methyl epoxides having the formula

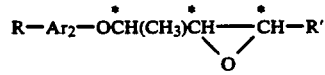

where Ar₂ is a phenylbenzoate, biphenyl phenylpyrimidine or phenyl pyridine, R is an alkyl or alkoxy group, and R' is an alkyl group containing 3 to 12 carbon atoms.

While a number of useful ferroelectric liquid crystal materials (both pure compounds and mixtures) have been reported, there is a growing need for FLC materials with varying properties of temperature range, tilt angle and switching speed for use in varied application. Further, there is a need for FLC dopants with varying mixing properties (which are dependent, at least in part, on chemical composition) for use in the preparation of FLC mixtures. FLC dopants which impart high polarization density to, and retain low viscosity in, such mixtures are of particular interest.

SUMMARY OF THE INVENTION

It is an object of the present invention to provide new classes of LC and FLC compounds having core groups derived from nicotinic acid.

The present invention provides pyridine and pyridine N-oxides of the formula:

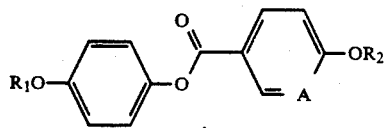

where A is N or N—O, wherein $R_1$ and $R_2$ independently of one another are straight chain or branched alkyl groups having from 1 to 20 carbons. For use as liquid crystal materials or in liquid crystal compositions, $R_1$ and $R_2$, which are alkyl groups, preferably contain 2 to 12 carbon atoms. For use as ferroelectric liquid crystal materials, or in ferroelectric liquid crystal compositions, one of $R_1$ or $R_2$ must be a chiral nonracemic group. $R_2$ is preferably the chiral nonracemic group. In particular, when A is N—O, it is preferred that $R_2$ is the chiral nonracemic group. Chiral nonracemic $R_2$ groups having from about 6 to 12 carbon atoms are preferred. When $R_2$ is the chiral nonracemic group, the $R_1$ group preferably has from 3 to 12 carbon atoms, and is preferably a straight chain alkyl group. A chiral nonracemic $R_2$ group which is a 1-methylalkyl group is more preferred, particularly when A is N-O. $R_2$ groups which are 1-methylalkyl groups preferably contain 5 to 12 carbon atoms.

In general, $R_1$ and $R_2$ can either or both be achiral groups, and $R_1$ and $R_2$ can either or both be chiral nonracemic groups.

In a specific embodiment, this invention provides chiral nonracemic, pyridine core compounds of the formula:

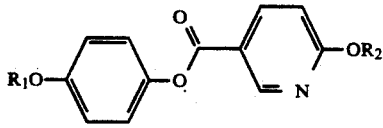

wherein $R_2$ is a chiral nonracemic group and wherein $R_1$ is an alkyl group having 6 to 12 carbon atoms. These compounds are of particular use in FLC applications as FLC compounds, host materials, or FLC dopants.

Preferred chiral nonracemic $R_2$ groups are those which impart high polarization in a smectic C phase. A number of such high polarization tail groups are known which may be incorporated as chiral nonracemic $R_2$ groups in compounds of the present invention.

Chiral nonracemic pyridine core compounds in which $R_2$ is a chiral nonracemic alkyl epoxide are specifically provided. Alkyl epoxide $R_2$ groups which are 2,3 alkyl epoxides are preferred. The 2,3 alkyl epoxide $R_2$ groups can be 1-substituted-2,3-alkyl epoxides, particularly 1-methyl substituted-2,3-alkyl epoxide groups. $R_2$ groups which are 2,3 alkyl epoxides having 4 to 10 carbon atoms are preferred. $R_2$ groups which are 1-methyl-2,3-epoxides having 5 to 11 carbon atoms are preferred. $R_2$ is preferably a trans-2,3-alkyl epoxide. $R_1$ groups preferably contain 8 to 12 carbon atoms.

In general, $R_2$ can have one or more asymmetric carbons. $R_2$, which is an alkyl epoxide, can have two or more asymmetric carbons.

In general, the pyridines and pyridine N-oxides of the present invention are useful as components of liquid crystal materials. In particular, chirally asymmetric molecules of this invention are useful as components of ferroelectric liquid crystal materials. Certain of these compounds can impart high polarization density and fast switching speeds to low polarization materials when mixed with such materials to form FLC compositions. Certain of the compounds of this invention can be employed as FLC host materials. Certain of the compounds of this invention exhibit liquid crystal phases, including smectic C phases.

DETAILED DESCRIPTION OF THE INVENTION

The general synthesis of chiral and achiral compounds of formula I and II having $R_1$ and $R_2$ groups that are alkyl groups is illustrated in Scheme I. The chlorine in 6-chloronicotinic acid (1) is displaced with alkoxide to give the alkoxy substituted nicotinic acid (2) which is then coupled to an alkoxy substituted phenol (3) to produce the pyridine-5-carboxylic acid phenyl esters (I). This route can be employed with $R_1$ and $R_2$ which are chiral or achiral and which are straight chain or branched alkyl groups. Synthesis of the pyridine N-oxide-5-carboxylic acid esters (II) where $R_1$ and $R_2$ are alkyl groups is achieved by oxidation of the corresponding pyridine esters (I) with m-chloroperbenzoic acid (MCPBA).

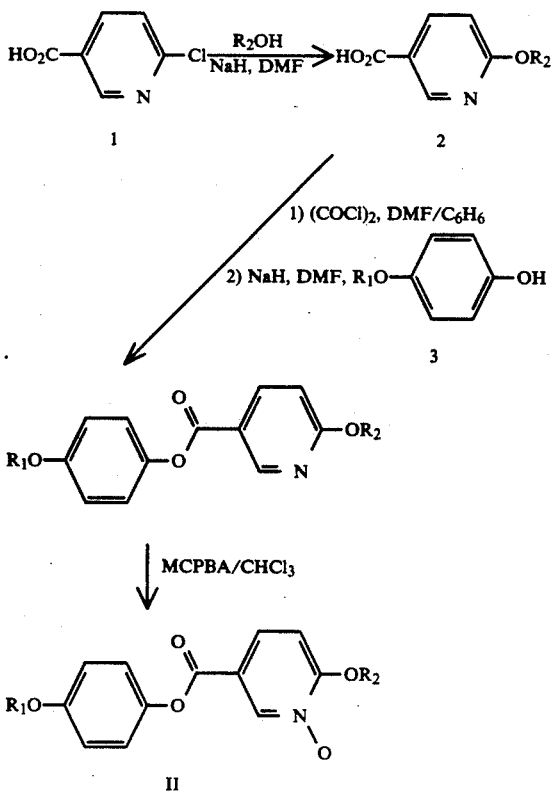

Compounds of formula I can also be produced as illustrated in Scheme II by Mistunobu coupling of the alcohol with the pyridone (6). The pyridone (6) is prepared by reaction of 6-chloronicotinic acid with benzyl alcohol to give the benzyloxy nicotinic acid (4), followed by coupling of compound 4 to the alkoxy phenol, (3) and debenzylation of the resulting coupling product (5). The pyridone (6) exists in equilibrium with a minor amount of the hydroxy nicotinic acid (7). Mitsunobu stereochemical coupling to produce compound I proceeds with inversion of configuration at the α-carbon of R₂O. Thus, coupling of 1(S)-methylheptyl alcohol to the pyridone (6) gives the 2-(1(R)-methylheptyloxy)-pyridine.

The procedure illustrated in Scheme II can also be used to prepare epoxy alcohol substituted pyridines. In this case R₂OH Scheme II is the epoxy alcohol, for example a 2,3-epoxy alcohol or a 1-methyl-2,3-epoxy alcohol. A variety of other substituted pyridines (I), in particular those in which R₂ is a chiral nonracemic group, can be prepared by use of the procedures illustrated in Schemes I and II, and in the Examples.

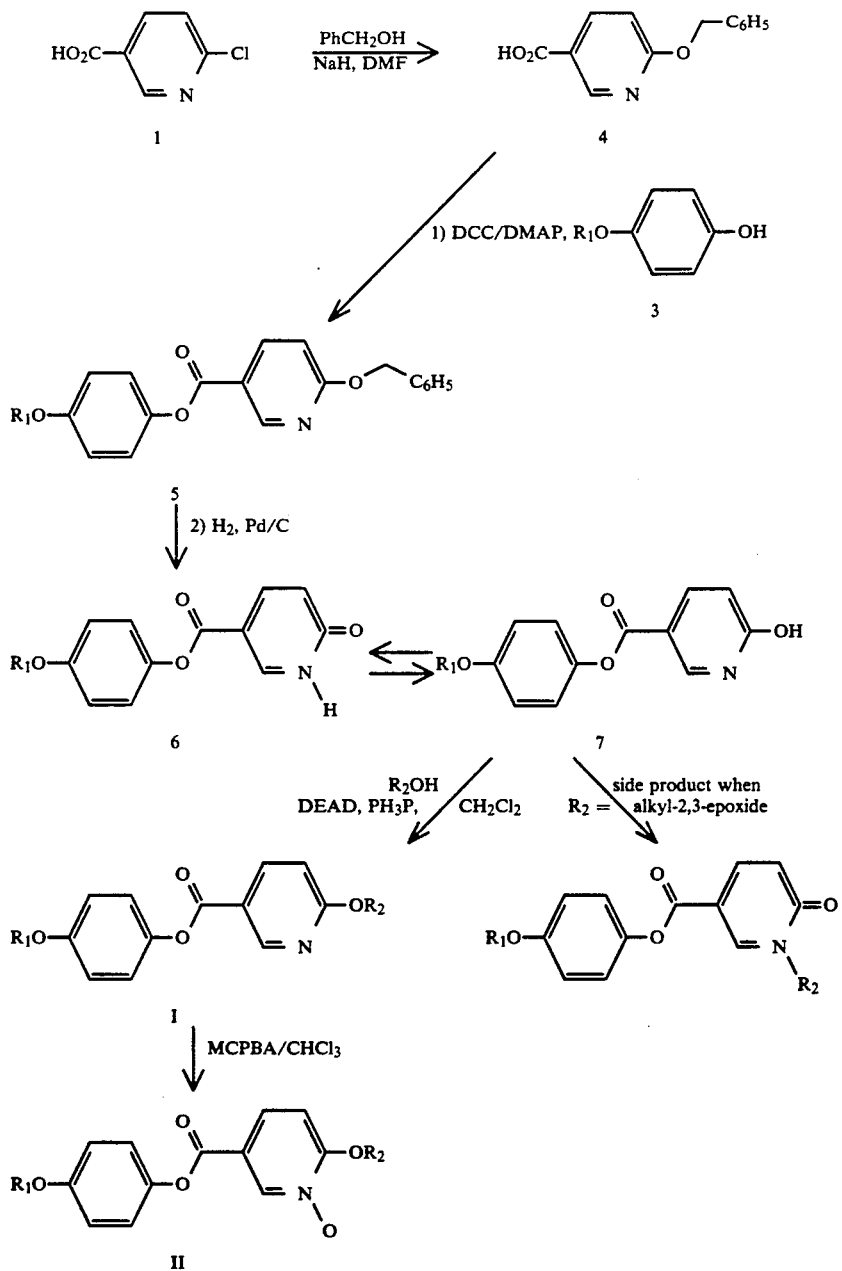

Synthesis of chiral nonracemic epoxy alcohols and 1-methyl-epoxy alcohols has been described in U.S. Pat. Nos. 4,638,073 and 4,705,874, and in U.S. patent application Ser. No. 360,397, which are all incorporated by reference herein.

In the case in which R₂ was an epoxy group, MCBA oxidization did not result in the desired pyridine N-oxide product. When R₂OH is an epoxy alcohol, its coupling to the pyridone (6) of Scheme II can result in the N-alkylation product as indicated.

The starting materials for synthesis of compounds of formula I or II by the procedures of Scheme I or II are readily available either as commercial products or by synthetic routes that are well known in the art. For example, alkoxy substituted phenols are either available from commercial sources or are readily prepared by known methods (see Neubert et al. (1978) Mol. Crys. Liq. Cryst. 44:197–210).

Table 1 summarizes phase diagrams of exemplary compounds of formula I or II, and polarization densities and tilt angles of some exemplary FLC mixtures of these compounds in W82. In Table 1, the phases are noted as X=crystal, I=isotropic liquid, A smectic A, C*=chiral smectic C, and phase transition temperatures are given in °C. Polarization densities (P) are given in $nC/cm^2$ and the magnitude of P was measured by integration of the dynamic current response to a surface stabilized ferroelectric liquid crystal cell on reversing the applied electric field using a slight modification of the standard methods of Martinot-Lagarde (1976) suora and Martinot-Lagarde (1977) suora. The polarization reversal current was measured after applying a triangular wave form (±15 volts) across a 2.5 μm (using Polyimide spacers) polymer aligned (DuPont Elvamide 8061) SSFLC cell (Patel, J. S. et al. (1986) J. Appl. Phys. 59:2355; Flatischler, K. et al., (1985) Mol. Cryst. Liq. Cryst. 131:21; Patel, J. S. et al. (1984) Ferroelectrics 57:137) with indium-tin oxide (ITO) conducting glass electrodes. The signal (current v. time) was digitized using a Sony/Tektronix 390AD programmable digitizer. The current waveform showed a peak characteristic of the polarization reversal; this current peak was integrated. Division of the value of this integration (charge) by the active area of the cell afforded the magnitude of ferroelectric polarization. For all measurements, the diameter of the ITO coated area of the cell was 0.50 inch. The sign of the polarization was determined directly from observation of molecular orientation in SSFLC cells upon application of electric fields. The optical tilt angle was determined by rotating the shear or polymer aligned cell until extinction was obtained. The polarity of the cell was reversed and the cell was rotated by a measured angle to obtain extinction again. The angle by which the cell was rotated is equal to $2\theta$. The tilt angle was obtained by dividing this angle by two. Tilt angles were measured at $T_c$-$T_x$, where $T_c$ and $T_x$ are the upper and lower transition temperatures for the C phase, respectively.

W82, 4'-(n-decyloxy)phenyl-4-(4(S)-methylhexyloxy)benzoate is known to possess an enantiotropic ferroelectric C* phase with very low polarization density of the order of −1 $nC/cm^2$ and slow electro-optical switching speed of the order of 3 msec (1 μm thick layer, SSFLC geometry, 15 V/μm driving voltage). Mixtures of the compounds of the present invention with W82 possess ferroelectric C* phases with higher polarization density and/or faster switching speeds than W82.

It is an important feature of this invention that the N-oxide cores containing compounds can, in some cases, exhibit enhanced polarization density. The effect of introduction of N or N-O ortho to the chiral nonracemic group into the core of an FLC compound on the polarization induced by that compound can be seen by comparing the FLC properties of the series of compounds in Table 2. All three of the compounds in Table 2 have the same tail group. All three of these compounds were examined in FLC mixtures with W82.

Introduction of N in the core ring at the position ortho to the chiral tail group decreases polarization density and changes its sign compared to that of the corresponding phenylbenzoate core compounds. Oxidation of the pyridine to the pyridine N-oxide results in a compound inducing a higher polarization density (same sign) than the phenylbenzoate. These results suggest that the dipoles of the N of the core, and the O of the chiral tail are opposed in the pyridine core molecule, and that the dipoles of the N-O of the core and that of the O are at least partially aligned in the N-oxide.

It should be noted that it is dipole orientation in the preferred conformations of the FLC molecule in the oriented smectic C phase that affects polarization density. It is important also to note that only the components of the dipoles normal to the tilt plane affect polarization. The structures of both the chiral asymmetric tail group as well as that of the core and any steric interaction between the groups will affect dipole orientation and the magnitude (and sign) of the polarization density.

As exemplified herein, the introduction of 1-substituted chiral nonracemic tail groups, particularly certain 1-methyl substituted chiral nonracemic tail groups into the N-oxide cores of the present invention result in high polarization materials.

Although not wishing to be bound by any theory, it is believed that the structures of Scheme II illustrate and interpret the differences in polarization observed with 1-methyl substituted chiral pyridines N-oxides and the corresponding pyridines. The structures illustrated in Scheme III assume that in the smectic C phase that the "crystal packing" forces exerted on an individual molecule by the rest of the molecules in the phase may be approximated by a binding site taking the shape of a bent cylinder. When confined to this site, the tails of the zig-zag shaped FLC molecules are less tilted than their cores. It is thus assumed that all C phases possess the same basic shape of binding site.

Scheme III compares the predicted conformations of 4'-decyloxyphenyl-2(1(S)-methylheptyloxy)pyridine-5-carboxylate and 4'-decyloxyphenyl-2(1(S)-methylheptyloxy)pyridine N-oxide-5-carboxylate with respect to the tilt plane. The conformations shown have a gauche bend at the $C(\alpha)$-$C(\beta)$ bond of the tail group, and the aromatic ring is oriented normal to the tilt plane. It has been assumed in this analysis that the lone pair on nitrogen is less sterically demanding than the ring H's. While arguments about steric size of lone pairs continue, there is considerable experimental and theoretical data supporting the conclusion that for substituted 1-alkoxypyridines, a gauche or syn periplanar conformation for the bond linking the ring to the tail is favored. Thus, with the 2-alkoxy substituted phenylpyridine ether core, it is predicted that the conformation with the methyl group on the same side as the N of the ring is preferred due to minimization of steric interactions with ring H's. In this conformation, the components of the dipole moments of the ring N and the tail ether bond normal to the tilt plane are opposed and subtract, resulting in a low polarization density. With the 2-alkoxy substituted pyridine N-oxide phenyl ester core, it is predicted that the conformation with the methyl group on the opposite side to the N-O of the ring is preferred due to minimization of steric interactions of the $CH_3$ and O. In this conformation, the components of the dipole moments of the ring NO bond and the tail ether bond normal to the tile plane are in the same direction and add, resulting in a high polarization density. The illustrations of Scheme III also predict that the sign of polarization of the pyridine N-oxide will be opposite to that of the pyridine. Similar polarization effects will be observed for other 1-substituted chiral tail groups positioned ortho to the N-O of the core, so long as the o-carbons of the tail group is also substituted with another group long enough, i.e. having greater than two carbon atoms, such that the long group is preferably oriented in the tilt plane. This requirement is clear when the properties of the 1-methylpropyloxy substituted pyridine N oxides are compared to those of the corresponding 1-methylheptyloxypyridine N-oxide. The 1-methylpropyloxy compound has low polarization density indicative of the absence of alignment of the components of the N-O and ether bond dipoles normal to the tilt plane. In the 1-methylpropyloxy compound, it is believed that no one conformation is significantly more preferred. This leads to an averaging of the components of the dipole normal to the tilt plane, and results in low polarization.

SCHEME III

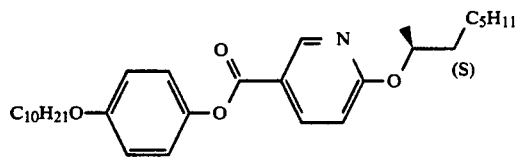

For a 24% mixture in W82
$P_{obs} = +1.9$ nC/cm$^2$
$P_{ext} = +11$ nC/cm$^2$ $\dfrac{P_{ext}}{\sin\theta} = +22$ nC/cm$^2$

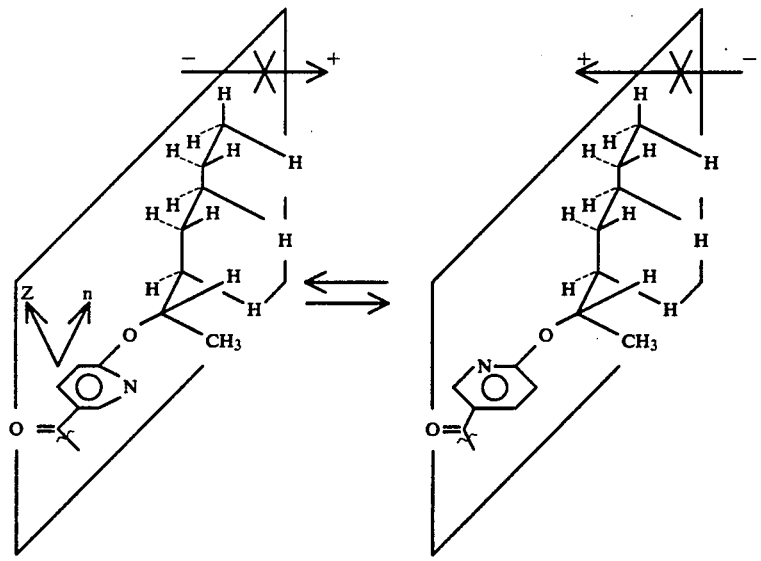

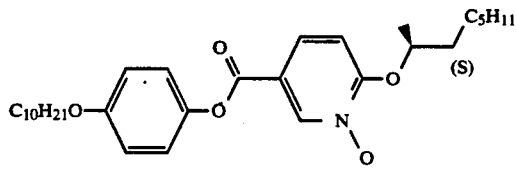

For an 18% mixture in W82
$P_{obs} = -20.9$ nC/cm$^2$
$P_{ext} = -120$ nC/cm$^2$ $\dfrac{P_{ext}}{\sin\theta} = -250$ nC/cm$^2$ -continued

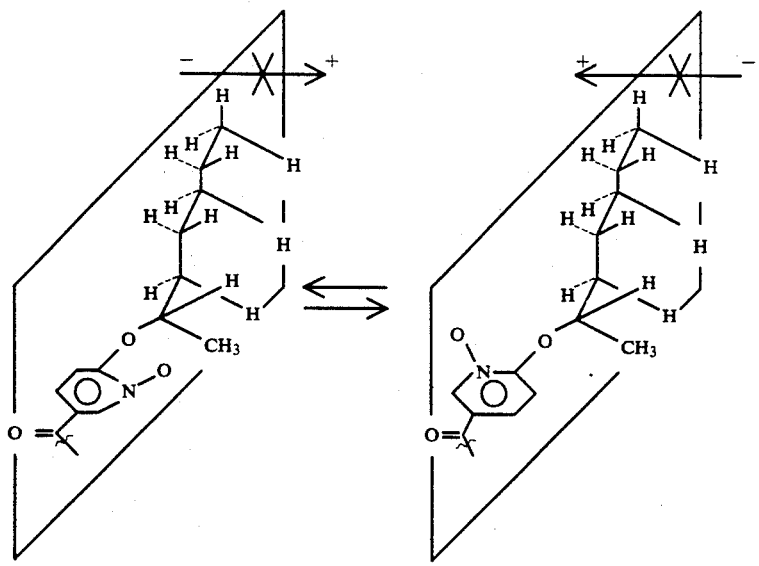

Variation in the structure, length and degree of branching in the $R_1$ and $R_2$ groups of compounds encompassed in formulas I and II can affect the liquid crystal properties of the pure material or mixtures containing them. For example, some of the chiral non-racemic compounds of the present invention may possess smectic C* phases while others do not and the characteristics of any such smectic C* phases (i.e. stability, temperature range) may vary.

The following examples illustrate the invention and are in no way intended to limit the scope of the invention.

EXAMPLES

EXAMPLE 1

Synthesis of 6-alkoxy- or 6-benzyloxynicotinic acid and the corresponding acid chlorides Preparation of alkoxy- or aryloxy nicotinic acids are exemplified by the following:

6-Benzyloxynicotinic acid

Oil-free NaH (1.9 g, ~5 eq.) was suspended in DMF (30 ml) and the suspension was cooled in an ice bath. Benzyl alcohol (8.6 ml, ~5.2 eq.) was added slowly to the suspension via syringe. The resulting reaction mixture was stirred at 0° C. for 20 min., after which it was transferred to a precooled (0° C.) solution of 6-chloronicotinic acid (2.5 g, 15.9 mmol) in DMF (30 ml). Additional DMF (20 ml) was added to the reaction mixture to facilitate stirring. The reaction mixture was refluxed for 2 hours. Aqueous acetic acid 5% (by volume) was added to the cooled reaction mixture, and the resultant acidic mixture was extracted (3x) with ethyl acetate. The organic layers were combined, washed with brine and the solvent was removed to give a yellow liquid, from which a white solid was obtained after addition of water. Recrystallization from acetone/water gave 6-benzyloxynicotinic acid (4, Scheme I, 88% yield) as colorless needles.

6-(1(S)-methylpropyloxy)

A procedure similar to that followed for the benzyloxynicotinic acid was used, employing 1(S)-methylpropanol as the starting alcohol. The reactions were carried out on a 1.59 mmol scale. Flash chromatography of the crude 6(1S-methylpropyloxy)nicotinic acid employing 10% hexane in ethyl acetate containing 1% (by volume) acetic acid gave a quantitative yield of the product as a brownish solid. The material (2, where $R_2 = 1(S)$-methylpropyl) was used without further purification.

6-(1(S)-methylheptyloxy)nicotinic acid

The same procedure followed for the methylpropyloxynicotinic acid was used employing 1(S)-methylheptanol as the starting alcohol. A quantitative yield of 6-(1(S)methylheptyloxy)nicotinic acid (2, where $R_2$ is 1(S)-methylheptyl was obtained as a brownish solid. The material was used without further purification.

Acid Chlorides

Acid chlorides were prepared by treating the corresponding nicotinic acids with oxalyl chloride (distilled, 2-3 eq.) with a catalytic amount of DMF in benzene overnight at room temperature.

EXAMPLE 2

Synthesis of 4'-alkoxyphenyl-2-(alkoxy)pyridine-5-carboxylates (I)

Coupling of alkoxy phenols with alkoxy nicotinic acids is illustrated by the following:

4'-decyloxyphenyl-2-1(S)-methylheptyloxy)pyridine-5-carboxylate

Oil-free NaH (98 mg, 2.5 eq.) was suspended in THF (10 ml). 4'-decyloxyphenol (3, where $R_1$ is $C_{10}H_{22}$, 398 mg, 1.59 mmol) dissolved in 10 ml of THF was added to the suspension via syringe. The reaction mixture was then stirred at room temperature for 15 min. 6-(1S-methylheptyloxy)nicotinic acid chloride was dissolved in THF (10 ml) and added via syringe to the reaction mixture which was thereafter stirred at room temperature for 17 hours. Water was then carefully added to the reaction mixture and the resulting slurry was extracted (3x) with ethyl acetate. The organic layers were combined, washed with 5% aqueous NaOH and brine, and dried over sodium sulfate. The solvent was removed to give a brownish solid which was initially purified by flash chromatography (5% by volume) ethyl acetate in hexane to give a 79% yield of 4′-decyloxyphenyl-2-(1S-methylheptyloxy)pyridine-5-carboxylate (I, where $R_1 = C_{10}H_{22}$ and $R_2 = 1(S)$-methylheptyl. The material could be recrystallized from ethanol to give white crystals.

4′-Decycloxyphenyl-2-(1(S)-methylpropyloxy)

A similar procedure to that described for the 1(S)-methylheptylcarboxylate was used employing 6-(1(S)-methylpropyloxy) nicotinic acid chloride. The reaction was run on a 1.7 mmol scale. 4′-Decyloxyphenyl-2-(1(S)-methylpropyloxy)pyridine 5-carboxylate (I, where $R_1 = C_{10}H_{22}$ and $R_2 = 1S$-methylpropyl) was obtained as a white solid recrystallized from ethanol.

EXAMPLE 3

Synthesis of the pyridine N-oxides

The synthesis of 4′-alkyloxyphenyl-2-(alkoxy)pyridine-5-carboxylate N-oxides, II where $R_2$ is an alkyl group is exemplified by the following:

4′-Decyloxyphenyl-2-(1(S)-methylpropyloxy pyridine-5-carboxylate N-oxide

4′-Decycloxyphenyl-2-(1(S)-methylpropyloxy)pyridine 5-carboxylate (106 mg, 0.248 mmol) was dissolved in 0.3 ml of dry CHCl$_3$ and the solution was cooled on an ice bath. A solution of m-chloroperbenzoic acid (97%, 67 mg, 1.5 eq.) in dry CHCl$_2$ (1 ml) was then added to the cooled solution. The resulting mixture was stirred in the dark as the temperature of the mixture was allowed to slowly rise to room temperature (over about 4 hours). Stirring was continued for an additional 15 hours. The reaction mixture was then filtered through basic aluminum oxide which was then washed with 25% (by volume) methanol in CHCl$_3$. The washings were combined with the filtrate and solvent was removed to give a solid residue. The residue was flash chromatographed (1% by volume methanol in ethyl acetate) to give 4-Decyloxyphenyl-2-(1(S)methylpropyloxy)pyridine (II, where $R_1 = C_{10}H_{22}$ and $R_2 = 1S$-methylpropyl) which was recrystallized from diethylether.

4′-Decyloxyphenyl-2-(1(S)-methylheptyloxy)pyridine-5-carboxylate N-oxide

4′-Decyloxphenyl-2-(1(S)-methylheptyloxy)pyridine-5-carboxylate was oxidized to the N-oxide II, where $R_1 = C_{10}H_{22}$ and $R_2 = 1(S)$-methylpropyl using the same procedure described above for the 1(S)-methylpropyloxypyridine N-oxide.

EXAMPLE 4

Synthesis of 4′-alkyloxyphenol-2-pyridine-5-carboxylates

The compounds of formula 5 are prepared as exemplified by the following:

4-Decyloxyphenyl-2-pyridine-5 carboxylate

6-Benzyloxynicotinic acid (2.0 g, 8.73 mmol) and 4-decyloxyphenol (2.4 g, 9.60 mmol) were suspended in CH$_2$Cl$_2$ (110 ml). Dicyclohexylcarbodimide (1.99 g, 9.66 mmol) was added to the suspension and the acid dissolved. 4-Pyrrolidinopyridine (130 mg) was added to the reaction mixture which was then stirred at room temperature for 25 hours. The reaction mixture was filtered, and solvent was removed from the filtrate to give a white solid. The solid was suspended in diethylether and the suspension was stirred for 30 minutes after which the remaining solids were removed and washed with ether. Solvent was removed from the combined washings and filtrate to give a white solid which was recrystallized from ethanol to give 4′-decyloxyphenyl-2-benzyloxypyridine-5-carboxylate.

This pyridine carboxylate (1.68 g, 3.64 mmol) was dissolved in CH$_2$Cl$_2$ (130 ml). Palladium on charcoal (678 mg) was then added and the reaction mixture was stirred under H$_2$ atmosphere (~5 psi) for 2.5 hours. The reaction mixture was filtered through Celite and the Celite was washed with hot ethyl acetate. The filtrate and washings were combined and solvent was removed to give 4-decyloxyphenyl-2-pyridone-5-carboxylate (5, where $R = C_{10}H_{22}$, 89% yield) as a white solid which was recrystallized from ethanol.

EXAMPLE 5

Chiral non-racemic 2,3-epoxy alcohols

The syntheses of the chiral epoxy alcohols is essentially as described in U.S. Pat. Nos. 4,638,073 and 4,705,874, and U.S. patent application Ser. No. 360,397, and are exemplified by the following:

1(S)-Methyl-2(S),3(S)-epoxyhexanol

Powdered, activated molecular sieves (4 Å, 1.80 g) were suspended in 205 ml of CH$_2$Cl$_2$ and the suspension was cooled to about $-30°$ C. (+)-Diisopropyltartrate (0.76 ml, 0.06 eq.) and titanium (IV) isopropoxide (0.88 ml, 0.05 eq.) was added to the cooled suspension via syringe. A 3.8 M CH$_2$Cl$_2$ solution of t-butylhydroperoxide (4.4 ml, 0.28 eq.) was then added dropwise to the suspension over 5 min. while the temperature of the suspension was maintained between $-20°$ C. and $-30°$ C. After 30 min., a CH$_2$Cl$_2$ solution of trans-3-hepten-2-ol was added dropwise to the reaction mixture The reaction mixture was then held in the freezer (at $-20°$ C.) for about 23 hours, after which it was warmed to $0°$ C. and poured onto a precooled ($0°$ C.) solution of ferrous sulfate heptahydrate (19 g) and tartaric acid (6 g) in 6 ml of water. The resulting solution was stirred at room temperature for 10 min. The organic and aqueous phases were separated and the aqueous phase was extracted ($2 \times 38$ ml) with ether. The organic layer and extracts were combined and vigorously stirred ($0°$ C., 1 hour) after addition of 6 ml of a 30% (w/v) solution of NaOH in brine. After addition of 30 ml of water, the phases were separated and the aqueous phase was extracted ($2 \times 30$ ml) with ether. The combined organic phases were dried over sodium sulfate. Evaporation of solvent, followed by flash chromatography of the residue (30% by volume ethyl acetate in hexane) gave a colorless liquid. The liquid was distilled to give 1(S)-methyl-2(S),3(S)-epoxyhexanol.

2(S),3(S)-epoxyhexanol

2(S),3(S)-epoxyhexanol was prepared by a procedure similar to that used for the preparation of the methylepoxy alcohol, except that 2 eq. of t-butylhydroperoxide was used. The reaction was run on a 10 mmol scale. Flash chromatography of the residue of the reaction resulted in 2(S),3(S)-epoxyhexanol.

EXAMPLE 6

Synthesis of 4'-alkloxyphenyl 4-(epoxyalkyloxy)pyridine-5-carboxylates, second method The compounds of formula I can also be prepared by coupling of a selected alcohol with 4-alkoxyphenyl-2-pyridone5-carboxylate, as exemplified by the following:

4'-Decyloxyphenyl-2-(1(R)-methyl-2(S),3(S)-epoxyhexyloxy)pyridone-5-carboxylate 4'-Decyloxyphenyl.2-pyridone-5-carboxylate (1.45 g, 3.90 mmol) and triphenylphosphine (1.23 g, 1.2 eq.) were suspended in $CH_2Cl_2$ (95 ml). A solution of 1(S)-methyl-2(S),3(S)-epoxyhexanol (0.52 g, 4.0 mmol) in $CH_2Cl_2$ (7 ml) was added to the suspension via syringe. The reaction mixture was heated to a gentle reflux to dissolve remaining solid. A solution of diethylazodicarboxylate (DEAD, 849 mg, 1.25 eq) in 15 ml of $CH_2Cl_2$ was then slowly added to the reaction mixture over about 25 min. The reaction mixture was then stirred at room temperature for 3 days. A small amount of water (5 drops) was added to the reaction ad stirring was continued for an additional hour. Solvent was then removed from the reaction mixture, the resulting residue was suspended in diethyl ether and the suspension was filtered through a silica gel pad. Solvent was removed from the filtrate and the residue solid was flash chromatographed (10% by volume ethyl acetate in hexane) to give 4'-decyloxyphenyl-2-(1(R)-methyl-2(S),3(S)-epoxyhexyloxy)pyridine-5-carboxylate, a colorless solid which was flash chromatographed a second time (20% ethyl acetate in hexane) to give a solid that was recrystallized from hexane. 4'-Decyloxyphenyl 1N-(1(R)-methyl-2(S),3(S)-epoxyhexyloxy) 2-pyridone-5-carboxylate is a side product of the foregoing synthesis.

4'-Decyloxyphenyl-2-(2(S),3(S)-epoxyhexyloxy)pyridine-5-carboxylate

This compound was prepared using the same procedure employed for the methyl epoxyhexyloxy derivative. 4'-Dexyloxyphenyl-2-(2(S),3(S)-epoxyhexyloxy)-pyridine-5-carboxylate was obtained in 4% yield and recrystallized from ethanol. The analogous pyridone carboxylate side product was also formed.

4-Decyloxyphenyl-2-(1(R)-methylheptyloxy)pyridine-5-carboxylate

This compound was prepared using the same procedure employed for the epoxy alcohol derivatized compounds of formula I. The reaction was run on a 2.5 mmol scale employing (S)-2-octanol (1.75 eq.). Flash chromatography (5% ethyl acetate in hexane) of the crude coupling product gave a 4'-dexyloxyphenyl-2-(1(R)-methylheptyloxy)pyridine-5-carboxylate (I where $R_1=C_{10}H_{22}$ and $R_2=1(R)$-methylheptyl) which was recrystallized from ethanol.

4'-Decyloxyphenyl-2(1(R)-methylpropyloxy)pyridine-5-carboxylate

This compound was prepared using the same procedure employed for the epoxy alcohol derivatized compounds of formula I. The reaction was run on a 0.539 mmol scale. The product was recrystallized from ethanol.

The invention has been described and illustrated by reference to several preferred embodiments, but it is not intended to limit the invention by doing so. For example, as noted above, enantiomers of chirally asymmetric compounds of the present invention will have the same magnitude of P, it is intended for chirally asymmetric compounds that the invention encompass both enantiomers of each compound. It is also intended that the invention include mixtures of the two enantiomers of the same formula in which there is an excess of one enantiomer. It is further intended that the invention encompass not only the LC compounds described specifically herein, but also compositions or formulations in which these compounds are admixed with each other or with other compounds including other LC and FLC materials.

TABLE 1

Phase Diagrams and Polarization Density of Chiral Nonracemic Pyridines and Pyridine N-Oxides

| Compound (Formula)[1] | Phase Diagram[2] | P |
|---|---|---|
| I where $R_2$ = 1(R)-methylpropyl | $X \underset{30}{\overset{55}{\rightleftarrows}} I$ | $P_{ext}$ = low (10% in W82) |
| I where $R_2$ = 1(R)-methylheptyl | $X \underset{25}{\overset{48}{\rightleftarrows}} I$ | $P_{ext}$ = −10.4 (31% in W82) $\Theta$ = 26.5 T−Tc = 29.2° $P_{obs}$ = −3.9 |
| I where $R_2$ = 1(S)-methylpropyl | $X \underset{32}{\overset{60}{\rightleftarrows}} I$ | |
| I where $R_2$ = 1(S)-methylheptyl | | $P_{ext}$ = +11 (23.8% in W82) $\Theta$ = 29° $P_{obs}$ = +1.9 |
| I where $R_2$ = 2(S),3(S)-epoxyhexyl | $X \underset{60}{\overset{70}{\rightleftarrows}} X' \underset{63}{\overset{73}{\rightleftarrows}} C \underset{\sim 80}{\overset{81}{\rightleftarrows}} A \overset{82}{\rightleftarrows} I$ | |

TABLE 1-continued

Phase Diagrams and Polarization Density of Chiral
Nonracemic Pyridines and Pyridine N-Oxides

| Compound (Formula)[1] | Phase Diagram[2] | P |
|---|---|---|
| I where $R_2$ = 1(R)methyl-2(S),3(S)-epoxyhexyl | X $\underset{37}{\overset{50}{\rightleftarrows}}$ I | |
| II where $R_2$ = 1(S)-methylpropyl | X $\underset{55}{\overset{87}{\rightleftarrows}}$ I | $P_{ext}$ = −1.6 (50% in W82) $\Theta$ = 28 T−Tc = −39.3 $P_{obs}$ = −1.3 |
| II where $R_2$ = 1(R)-methylheptyl | X $\underset{54}{\overset{76}{\rightleftarrows}}$ I | $P_{ext}$ = +120 (18% in W82) $\Theta$ = 28.8° |

[1] In all cases $R_1$ = $C_{10}H_{21}$
[2] Temperatures given in °C., X = crystal, C = smectic, A = smectic A, I = isotropic.

TABLE 2

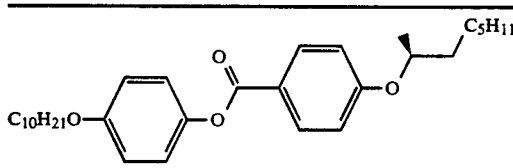

For a 25% mixture of the parent structure in W82

$P_{obs}$ = −11.5 nC/cm$^2$ $P_{ext}$ = −49 nC/cm$^2$ $\dfrac{P_{ext}}{\sin\theta}$ = −98 nC/cm$^2$

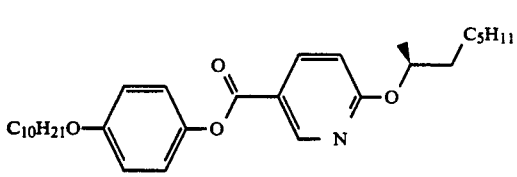

For a 24% mixture of the pyridine in W82

$P_{obs}$ = +1.9 nC/cm$^2$ $P_{ext}$ = +11 nC/cm$^2$ $\dfrac{P_{ext}}{\sin\theta}$ = +22 nC/cm$^2$

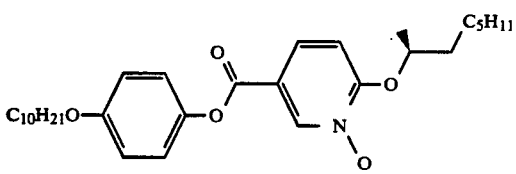

For an 18% mixture in W82

$P_{obs}$ = −20.9 nC/cm$^2$ $P_{ext}$ = −120 nC/cm$^2$ $\dfrac{P_{ext}}{\sin\theta}$ = −250 nC/cm$^2$

We claim:

1. A liquid crystal compound of the formula:

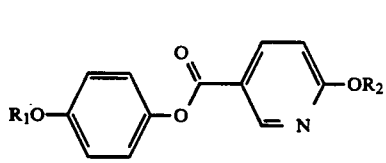

wherein $R_1$ and $R_2$, independently of one another, are straight chain or branched alkyl groups having from 1 to 20 carbon atoms.

2. The compound of claim 1 wherein $R_1$ and $R_2$ independently of one another are straight chain or branched alkyl groups having from 2 to 12 carbon atoms.

3. The compound of claim 1 wherein one of either $R_1$ or $R_2$ is a chiral nonracemic alkyl group.

4. The compound of claim 1 wherein $R_1$ is an alkyl group having from 6 to 12 carbon atoms.

5. The compound of claim 1 wherein $R_2$ is an alkyl group having from 3 to 12 carbon atoms.

6. A liquid crystal compound of the formula:

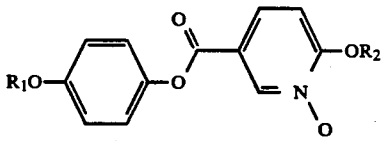

wherein $R_1$ and $R_2$, independently of one another, are straight chain or branched alkyl groups having from 1 to 20 carbon atoms.

7. The compound of claim 6 wherein $R_1$ and $R_2$ independently of one another are straight chain or branched alkyl groups having from 2 to 12 carbon atoms.

8. The compound of claim 6 wherein one of either $R_1$ or $R_2$ is a chiral nonracemic alkyl group.

9. The compound of claim 6 wherein $R_1$ is an alkyl group having from 6 to 12 carbon atoms.

10. The compound of claim 6 wherein $R_2$ is an alkyl group having from 3 to 12 carbon atoms.

11. A chiral nonracemic ferroelectric liquid crystal compound of the formula

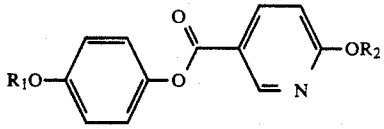

wherein R₂ is a chiral nonracemic alkyl or epoxyalkyl group, and wherein R₁ is an alkyl group having from 1 to 20 carbon atoms.

12. The compound of claim 11 wherein R₁ is an achiral alkyl group having 6 to 12 carbon atoms and R₂ is a chiral nonracemic alkyl group having from 3 to 12 carbon atoms.

13. The compound of claim 11 wherein R₂ is a chiral nonracemic alkyl group which is a 1-methyalkyl group.

14. The compound of claim 13 wherein R₂ has 5 or more carbon atoms.

15. The compound of claim 13 wherein R₂ is a chiral nonracemic 1-methylheptyl group.

16. The compound of claim 13 wherein R₂ is a chiral nonracemic 1-methylpropyl group.

17. The compound of claim 13 wherein R₁ is a straight chain alkyl group having from 6 to 12 carbon atoms.

18. The compound of claim 13 wherein R₂ is a chiral nonracemic 1-methylheptyl group, and R₁ is an n-decyl group.

19. The compound of claim 11 wherein R₂ is an alkyl epoxide group.

20. The compound of claim 19 wherein R₂ is a 2,3-alkyl epoxide group.

21. The compound of claim 20 wherein R₂ is a 1-methyl-2,3-alkyl epoxide group.

22. The compound of claim 21 wherein R₂ contains 5 to 11 carbon atoms.

23. The compound of claim 20 wherein R₂ contains 4 to 10 carbon atoms.

24. The compound of claim 22 wherein R₂ is a chiral nonracemic 2,3-epoxy hexyl group.

25. The compound of claim 24 wherein R₁ is an n-decyl group.

26. The compound of claim 23 wherein R₂ is a chiral nonracemic 1-methyl-2,3-epoxy hexyl group.

27. The compound of claim 26 wherein R₁ is an n-decyl group.

28. An chiral nonracemic ferroelectric liquid crystal compound of formula:

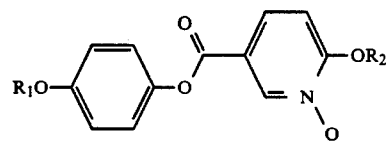

wherein R₂ is a chiral nonracemic alkyl or epoxyalkyl group, and wherein R₁ is an alkyl group having from 1–20 carbon atoms.

29. The compound of claim 28 wherein R₁ is an alkyl having from 6 to 12 carbon atoms.

30. The compound of claim 28 wherein R₂ is an alkyl group having from 3 to 12 carbon atoms.

31. The compound of claim 28 wherein R₁ is an achiral alkyl group having 6 to 12 carbon atoms, and R₂ is a chiral nonracemic alkyl group having from 3 to 12 carbon atoms.

32. The compound of claim 28 wherein R₂ is a chiral nonracemic alkyl group which is a 1-methylalkyl group.

33. The compound of claim 32 wherein R₂ has 5 or more carbon atoms.

34. The compound of claim 32 wherein R₂ is a chiral nonracemic 1-methylheptyl group.

35. The compound of claim 32 wherein R₂ is a chiral nonracemic 1-methylpropyl group.

36. The compound of claim 32 wherein R₁ is a straight chain alkyl group having from 6 to 12 carbon atoms.

37. The compound of claim 32 wherein R₂ is a chiral nonracemic 1-methylheptyl group, and R₁ is an n-decyl group.

* * * * *

UNITED STATES PATENT AND TRADEMARK OFFICE
CERTIFICATE OF CORRECTION

PATENT NO. : 5,145,601

DATED : Sep. 8, 1992

INVENTOR(S) : Bengt Otterholm; David M. Walba

It is certified that error appears in the above-identified patent and that said Letters Patent is hereby corrected as shown below:

Title Page: Item [57], fourth line from bottom of text, please rewrite "n-oxides" as --N-oxides--. At column 4, line 10, please rewrite "alkoxy" as --alkoxyl--. At column 8, about line 34, please rewrite "<———" as -- <——— --. At column 9, line
———>                                   ——>
13, please rewrite "A smectic" as --A = smectic--. At column 9, line 21, both occurrences, please rewrite "suora" as --supra--. At column 10, line 68, please rewrite "tile" as --tilt--. At column 11, line 7, please rewrite "o-carbons" as --α-carbons--. At column 13, about line 15, please rewrite "<———" as
                                                                ———>
--  <—— --. At column 13, line 65, please insert
———>
--nicotinic acid-- after "6-(1-(S)-methylpropyloxy)". At column line 10, please insert--pyridine-- before "-5-carboxylate" after "4'-Decycloxyphenyl-2-(1(S)-methylpropyloxy)". At column 15, line 32, please rewrite "CHCl$_2$" as --CHCl$_3$--. At column 15, line 58, please rewrite "4'-alkyloxyphenol-" as --4'-alkyloxyphenyl- --. At column 21, line 17 (line 2 of claim 13), please rewrite "methyalkyl" as --methylalkyl--.

UNITED STATES PATENT AND TRADEMARK OFFICE
CERTIFICATE OF CORRECTION

PATENT NO. : 5,145,601
DATED : Sep. 8, 1992
INVENTOR(S) : Bengt Otterholm; David M. Walba It is certified that error appears in the above-indentified patent and that said Letters Patent is hereby corrected as shown below:

Column 14, lines 62-63, and column 15, lines 5-6, "15-methylheptyloxy" should read --1(s) methylheptyloxy--.

Signed and Sealed this

Fifteenth Day of March, 1994

Attest:

BRUCE LEHMAN

Attesting Officer

Commissioner of Patents and Trademarks